United States Patent
Tillotson

(10) Patent No.: US 8,471,730 B2
(45) Date of Patent: Jun. 25, 2013

(54) SYSTEMS AND METHODS FOR EARLY DETECTION OF AIRCRAFT APPROACH TO VOLCANIC PLUME

(75) Inventor: Brian J. Tillotson, Kent, WA (US)

(73) Assignee: The Boeing Company, Chicago, IL (US)

( * ) Notice: Subject to any disclaimer, the term of this patent is extended or adjusted under 35 U.S.C. 154(b) by 421 days.

(21) Appl. No.: 12/883,290

(22) Filed: Sep. 16, 2010

(65) Prior Publication Data
US 2012/0068862 A1 Mar. 22, 2012

(51) Int. Cl.
G08B 21/00 (2006.01)
G01W 1/00 (2006.01)

(52) U.S. Cl.
USPC ............... 340/945; 340/963; 340/601; 702/3; 702/4

(58) Field of Classification Search
USPC .............. 340/945, 947, 963, 964, 601; 701/7, 701/13, 16; 702/3, 4; 250/308, 360.1
See application file for complete search history.

(56) References Cited

U.S. PATENT DOCUMENTS

| | | | |
|---|---|---|---|
| 3,173,004 A * | 3/1965 | McKenzie | ............... 250/360.1 |
| 5,654,700 A | 8/1997 | Prata et al. | |
| 6,809,648 B1 | 10/2004 | Fleming | |
| 7,034,935 B1 | 4/2006 | Kruzelecky | |
| 7,383,131 B1 | 6/2008 | Wey et al. | |
| 7,609,463 B2 | 10/2009 | Tsao | |
| 7,689,328 B2 | 3/2010 | Spinelli | |
| 7,735,352 B2 | 6/2010 | Alm et al. | |
| 7,743,641 B2 | 6/2010 | Bailey et al. | |
| 2007/0120693 A1 | 5/2007 | Vij | |
| 2008/0099630 A1 | 5/2008 | Parikh et al. | |
| 2009/0272270 A1 | 11/2009 | McGill et al. | |
| 2012/0191350 A1 * | 7/2012 | Prata et al. | ........................ 702/3 |

FOREIGN PATENT DOCUMENTS

| | | |
|---|---|---|
| GB | 2451278 A | 1/2009 |
| JP | 2007193773 A | 8/2007 |
| WO | 2011151462 A1 | 12/2011 |

OTHER PUBLICATIONS

Search report from European Patent Application No. EP 11181701, European counterpart to U.S. Appl. No. 12/883,290, report dated Jan. 17, 2012.

C.A.M. Brenninkmeijer et al., Civil Aircraft for the regular investigation of the atmosphere based on an instrumented container: The new CARIBIC system, Atmos. Chem. Phys., 7 (2007), pp. 4953-4976.

* cited by examiner

*Primary Examiner* — Van T. Trieu
(74) *Attorney, Agent, or Firm* — Ostrager Chong Flaherty & Broitman P.C.

(57) ABSTRACT

Onboard systems and methods for early detection that an aircraft is approaching a volcanic (ash) plume or a gas plume having a concentration of a volcanic gas which would be toxic to humans. The detection method generally comprises the steps of measuring the concentration of one or more volcanic gases in air circulating in a space inside an aircraft and generating an alarm when one or more measured volcanic gas concentrations exceed a respective user-specified threshold or when a pattern of volcanic gas concentration is recognized with a user-specified confidence level. These systems are configured so that the alarm indicates the proximity of dangerous levels of either a volcanic gas or of volcanic ash. In particular, the detection system utilizes the air circulating through an aircraft cabin or cockpit to enable use of low-cost, carry-on electronic devices.

20 Claims, 4 Drawing Sheets

US 8,471,730 B2

SYSTEMS AND METHODS FOR EARLY DETECTION OF AIRCRAFT APPROACH TO VOLCANIC PLUME

BACKGROUND

This invention generally relates to systems and methods for sensing when an aircraft is approaching a volcanic plume. In particular, this invention relates to systems and methods for onboard detection of patterns of ambient gas concentrations to infer the presence of a volcanic plume before passengers and crew are affected.

As used herein, the term "volcanic plume" means a cloud of volcanic ash, the term "volcanic gases" means gases given off by active volcanoes, and the term "gas plume" means a plume of a volcanic gas. Dispersed volcanic gases disposed outside the volume occupied by a volcanic ash cloud are not included as part of the "volcanic plume" as the latter term is used herein.

Volcanic ash can pose a hazard to flying jet aircraft, threaten the health of people and livestock, damage electronics and machinery, and interrupt power generation and telecommunications. Volcanic ash comprises tiny jagged particles of rock and natural glass blasted into the air by a volcano. Wind can carry ash thousands of miles, affecting far greater areas than other volcano hazards.

Volcanic plumes present two problems for aircraft: (a) engine shutdown due to ash; and (b) aircraft damage and/or crew and passenger injury due to ash and corrosive gases. Volcanic ash particles are extremely abrasive. They are jagged particles of rock and glass that can cause rapid wear to the internal workings of jet engines. More important, high temperatures in some parts of jet engines can melt the ash; it then re-solidifies on cooler parts of the engine, forming a layer that blocks airflow, interferes with moving parts, and eventually shuts down the engine.

Another issue is the potentially harmful effects of elevated concentrations of $SO_2$ and sulfate aerosol in ash-poor clouds on aircraft and avionics. In addition, volcanic ash particles, with sulfuric acid adhered thereto, are tiny enough to travel deep into the lungs of human beings, which may be harmful and potentially fatal to people.

Various known solutions for detecting and avoiding a volcanic plume during flight of an aircraft have certain disadvantages. First, in daytime clear weather, pilots can see and avoid the visually distinctive cloud from an erupting volcano. However, volcanic plumes are often encountered during nighttime and/or embedded within other clouds. Therefore, visual detection is not always effective.

Second, for volcanoes that are well monitored, sensors or people on the ground can quickly observe an eruption and report it to flight safety authorities such as the FAA. In these cases, a notice to airmen is issued. However, many remote volcanoes around the world are still not well instrumented and can erupt without immediate detection. Even after detection, the mechanism to issue a notice to airmen imposes a delay for processing and distribution, during which an unwarned aircraft may encounter the plume.

Third, a few satellites are capable of detecting volcanic plumes from orbit, based on the sulfur dioxide spectra, the thermal infrared emission, visible ash clouds, or a combination of these. When a satellite detects a volcanic plume, a notice to airmen is issued. However, satellite observations are not continuous. An eruption that occurs between satellite passes may go undetected for 6 to 12 hours, which is more than enough time for aircraft to encounter the plume. The period of non-detection may go on longer for small eruptions or during overcast conditions. Even after detection, the mechanism to issue a notice to airmen imposes a delay for processing and distribution, during which an unwarned aircraft may encounter the plume.

Fourth, onboard systems for detecting the presence of a volcanic plume during flight have been proposed in various patents. For example, U.S. Pat. No. 5,654,700, entitled "Detection System for Use in an Aircraft," proposes a system that would detect a volcanic ash cloud ahead of an aircraft by monitoring infrared radiation that traverses the ash cloud; and U.S. Pat. No. 7,383,131, entitled "Airborne Volcanic Ash Cloud and Eruption Detection System and Method," proposes the provision of an onboard computer having program logic "configured to correlate the location of a volcano from [a] database with the presence of lightning from [a] lightning detector and a volcanic ash plume from [a] weather radar."

There exists a need for a system that will detect and alert an aircraft to avoid volcanic plumes, which may stretch for hundreds of miles through a variety of atmospheric conditions, including clouds. Detecting plumes embedded in clouds is of particular interest, since these cannot be visually detected by pilots. Repeated fly-throughs of even dilute plumes can cause long-term damage to aircraft, including structures, engines and electrical equipment, because of the corrosive nature of the hydrogen sulfide ($H_2S$) and sulfur dioxide ($SO_2$) gases in plumes.

BRIEF SUMMARY

The invention solves the problem of detecting the approach of an aircraft to a volcanic plume having an ash concentration which is dangerous to aircraft, including a volcanic plume that is embedded in clouds, or to a gas plume having a volcanic gas concentration which is dangerous (i.e., toxic) to humans. The detection system is installed onboard an aircraft. The onboard system comprises one or more electronic gas sensors that are exposed to incoming cockpit or cabin air. This exposes the sensors to roughly the same gas concentrations as are present in the outside air. Each sensor measures the concentration of a respective gas in the incoming air which is moderately abundant in nearly all volcanic plumes, such as $H_2$, $CO_2$, $SO_2$ and $H_2S$. The detection system measures the concentration of one or more volcanic gases in air circulating in a space inside an aircraft and then generates a perceptible alarm when one or more measured volcanic gas concentrations exceed a respective user-specified threshold or when a pattern of volcanic gas concentration is recognized with a user-specified confidence level. These systems are configured so that the alarm indicates the proximity of dangerous levels of either a volcanic gas or of volcanic ash. In particular, the system exploits the different diffusion rates of volcanic gases to infer the proximity of a volcanic plume by enabling the measurement of concentrations of volcanic gases which have diffused beyond the extent of the volcanic (i.e., ash) plume.

Optionally, the alarm may include an estimated range to a point of interest in the volcanic plume. A volcanic plume has substantial volume; it is not a single point in space. As used herein, the term "range to a point of interest in the plume" means the distance from the aircraft to a particular point along the axis or on the surface (i.e., outer boundary) of the plume's geometry. Examples of points of interest include the point along the volcanic plume's axis nearest to the aircraft, the nearest point on the volcanic plume's outer surface or boundary at which ash density is high enough to damage aircraft, and the point on the volcanic plume's surface at which ash density is high enough to damage aircraft and which would be intersected by the aircraft were it to continue on its present course.

For navigation and modeling, typically the volcanic plume can be assumed to be generally conical and the axis of the conical volcanic plume can be used as the reference. Likewise the respective gas plumes can be assumed to be generally conical, all of the cones (including the volcanic plume) having a common axis. For aviation safety, the pilot should be advised concerning the estimated range (measured along his current flight path) to the outer surface of the ash cloud, i.e., the two-dimensional curve in three-dimensional space at which the density of volcanic ash is just high enough to damage an aircraft.

Other aspects of the invention are disclosed and claimed below.

BRIEF DESCRIPTION OF THE DRAWINGS

Reference will hereinafter be made to the drawings in which similar elements in different drawings bear the same reference numerals.

DETAILED DESCRIPTION

Figure 1:
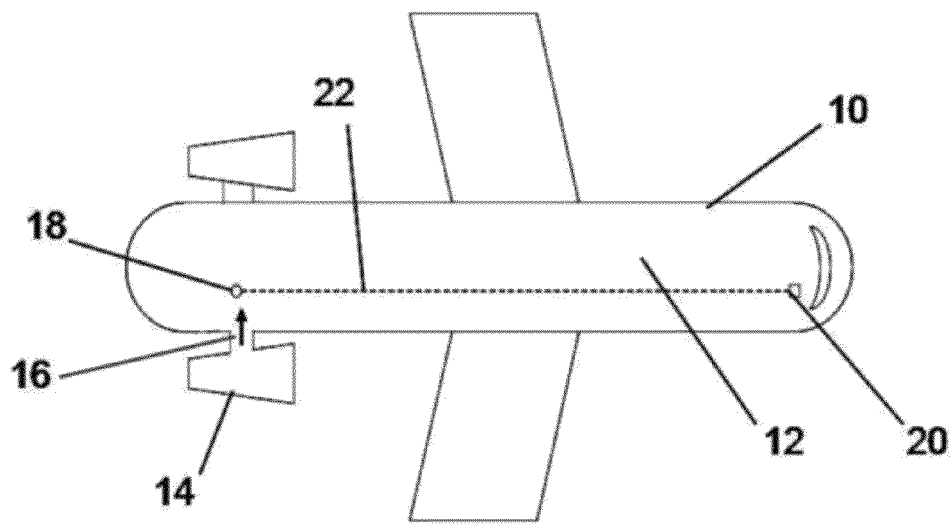
FIG. 1 is a diagram showing the location of a gas sensor onboard an airplane in accordance with one embodiment of the invention.

Various embodiments of a detection system that measures the concentrations of one or more volcanic gases onboard an airplane will now be disclosed. The detection method generally comprises the steps of measuring the concentration of one or more volcanic gases in air circulating in a space inside an aircraft and generating an alarm when one or more measured volcanic gas concentrations exceed a respective user-specified threshold or when a pattern of volcanic gas concentration is recognized with a user-specified confidence level. These systems are configured so that the alarm indicates the proximity of dangerous levels of either a volcanic gas or of volcanic ash. In particular, the detection system utilizes the air circulating through an aircraft cabin or cockpit to enable use of low-cost, carry-on electronic devices that can be deployed and used by aircraft operators without FAA certification.

The detection systems disclosed herein comprise one or more electronic sensors that measure concentrations of respective volcanic gases, such as hydrogen, carbon dioxide, sulfur dioxide and hydrogen sulfide. The required measurement sensitivity and precision are comparable to those used in industrial facilities to detect hazardous gases. Examples of such sensors are a gas chromatograph or an infrared spectrometer. Suitable gas chromatographs are disclosed in U.S. Pat. Nos. 7,735,352 and 7,743,641 and U.S. Patent Application Publ. No. 2009/0272270, the disclosures of which are incorporated by reference herein in their entirety. Suitable infrared spectrometers are disclosed in U.S. Pat. Nos. 7,034,935 and 7,609,463, the disclosures of which are incorporated by reference herein in their entirety.

In accordance with some embodiments, the system comprises an ensemble of sensors, each sensor measuring the concentration of a respective one of these volcanic gases. In accordance with one embodiment, when the system detects one of the volcanic gases at a concentration higher than some user-specified threshold, the system issues an audible or visible alert to the pilot. In accordance with another embodiment, the system detects a state wherein two or more volcanic gases are at concentrations higher than respective user-specified thresholds and then issues an audible or visible alert to the pilot. Alternatively, successive alarms could be generated as the first and second gas concentrations exceed their respective thresholds. The thresholds can be selected such that the alarm is generated before the measurements indicate a concentration of a volcanic gas that is dangerous to humans. Alternatively, the threshold can be selected such that measured concentration of the volcanic gas indicates the proximity (not the presence) of a volcanic (i.e., ash) plume. Preferably, the lesser of the two thresholds is selected by the user.

In accordance with further embodiments, the ensemble of sensors is augmented with a computer that monitors the measured gas composition over time. In accordance with one embodiment, the computer compares the temporal pattern of one measured gas concentration to a reference pattern representing a temporal pattern that would be expected when an aircraft approaches a volcanic plume, and then activates an alarm when the measured and reference temporal patterns match to a degree that exceeds a user-specified confidence level. In accordance with another embodiment, the computer compares the temporal patterns of two or more measured gas concentrations to respective reference patterns representing respective temporal patterns that would be expected when an aircraft approaches a volcanic plume, and activates an alarm when the measured and reference temporal patterns for each volcanic gas match to a degree that exceeds a user-specified confidence level. In either case, the alarm may optionally include an estimated range to a point of interest in the volcanic (i.e., ash) plume.

Typically, the range to a point of interest in the volcanic plume can be estimated by a computer using a least squares error minimization algorithm to fit the measurements of gas concentration at various locations to the expected gas distribution. This is standard curve-fitting in three spatial dimensions. One may include a fourth dimension, time, for the curve fitting if the measurements are separated by an interval that is long relative to the dynamics of the volcanic plume, e.g., more than a few minutes for cases where there is strong wind shear between different altitudes within a probable volcanic plume.

In accordance with a simple embodiment, the curve to fit is a Gaussian distribution of gas concentration versus range from the plume axis. The distance scale factor $\sigma$ increases with time from emission, which typically means it increases with distance downstream in the plume. The distance scale factor is also different for each gas: larger for gases with large diffusion coefficients, e.g., hydrogen, and smaller for gases with small diffusion coefficients, e.g., sulfur dioxide. Thus the concentration of gas i at location (x, y, z) is modeled as:

$$C_i(x, y, z) = C_{0i}\left(\frac{1}{\sqrt{2\pi\sigma^2}}e^{-\frac{y^2+z^2}{2\sigma^2}}\right)$$

where $\sigma = D_1 x/v$, $C_{0i}$ is a coefficient proportional to the rate of emission for gas i, $D_i$ is the diffusion coefficient for gas i, x is distance downwind from the plume's origin, y is distance crosswind from the plume axis, z is vertical distance from the plume axis, and v is the wind speed. (The term x/v is equal to the time from emission, so time need not be explicitly modeled.)

However, until the source of the volcanic plume is located, the coordinate system (x, y, z) is unknown. Instead, the system measures concentrations at locations specified in some Earth-relative coordinates (x', y', z'). The system comprises a computer that minimizes the total squared error between the modeled concentration curve of each gas, indexed by i, and the concentration measurements, indexed by j:

Sum squared error=$\Sigma_{ij}$[modeled $C_i(x'_j, y'_j, z'_j)$–measured $C_i(x'_j, y'_j, z'_j)$]$^2$ To minimize the error, the sum squared error is differentiated with respect to the plume's origin (the tip of the cone) in Earth-relative coordinates $(x'_0, y'_0, z'_0)$ and the emission rate coefficients $C_{0i}$, and the computer solves for the value of $(x'_0, y'_0, z'_0, C_{0i})$, where the derivative is zero with respect to all four parameters. This assumes wind direction and speed are known, e.g., via data from the airplane's flight control system, so one can a priori fix the rotational transformation from Earth-relative coordinates (x', y', z') to the wind-oriented coordinates (x, y, z). In embodiments where wind data is not available or reliable, the sum squared error is also differentiated with respect to the wind direction $\theta$ and wind speed v, then one solves for the value of $(x'_0, y'_0, z'_0, C_{0i}, \theta, v)$ that zeroes all derivatives.

For more sophisticated embodiments, additional inputs such as sensor precision, wind shear, locations of volcanoes known to be active or dormant, relative gas compositions of prior eruptions, and variation of diffusion coefficients with altitude are used to more precisely model or constrain the distribution of gas concentrations in a gas plume. Appropriate methods for handling these complex (and often probabilistic) inputs include Monte Carlo analyses or the maximum entropy method.

In 1994, Symonds et al. published an article in *Reviews in Mineralogy*, Vol. 30, entitled "Volcanic-Gas Studies: Methods, Results, and Applications," which article included a list of equilibrium compositions of high-temperature, low-pressure (1 bar) gases from various volcanoes. The data presented shows that the composition of gases from volcanoes around the world varies widely, but hydrogen sulfide and sulfur dioxide are at least moderately abundant in nearly all of them. (Note that the most abundant gas, $H_2O$, will quickly precipitate out as the plume cools. The relative abundance of hydrogen sulfide will therefore increase.) The concentrations of hydrogen, hydrogen sulfide, carbon dioxide and sulfur dioxide in the published volcanic-gas samples fell in the following ranges (mole %): 0.30-2.80 ($H_2$); 0.04-1.12 ($H_2S$); 3.15-48.90 ($CO_2$); and 0.2089-47.70 ($SO_2$).

An important difference among the four gases is their diffusion coefficients in air. The diffusion coefficient of a dilute gas is roughly inversely proportional to (a) the square root of molecular mass and (b) the square of the mean molecular radius. The molecular masses of the four gases are 2 for hydrogen, 34 for hydrogen sulfide, 44 for carbon dioxide, and 64 for sulfur dioxide. The molecular radii are ranked in the same order. Therefore, the gases diffuse at substantially different rates, e.g. hydrogen diffuses more than six times faster than sulfur dioxide. In a preferred embodiment, the invention relies on these different diffusion rates to provide robust detection of the proximity of a volcanic plume and a robust estimate of the rate at which an airplane is approaching the volcanic plume. (Volcanic ash, the most serious hazard, diffuses orders of magnitude slower than any gas. It spreads primarily by wind currents and gravity.)

In accordance with a simple embodiment depicted in FIG. 1, a hand-portable electronic gas sensor 18 configured to measure the concentration of a volcanic gas is carried onboard an airplane 10 by a crew member and stowed in a position inside the cabin 12 where they are exposed to incoming cabin air (i.e. not stowed in an overhead bin with limited air circulation.) In the embodiment shown in FIG. 1, the gas sensor 18 is placed near a cabin air inlet 16 that is in flow communication with air entering a jet engine 14. Alternatively, an ensemble of gas sensors configured to measure the concentration of respective volcanic gases can be placed near the cabin air inlet. In accordance with further alternative embodiments, one or more gas sensors can be stowed in the cockpit, e.g., behind the pilot's seat. In flight, the airplane's air circulation system draws in air from outside the airplane and circulates it into the cockpit and cabin. This exposes the gas sensors to roughly the same gas concentrations as are present in the outside air.

The usual way to sense gases outside the airplane would be to install a substantially permanent sensor that penetrates the airplane's skin. A penetration and a permanently installed instrument would each impose a great deal of cost and delay for engineering and FAA certification, plus would require the use of expensive hardware suitable for exposure to the external environment of the airplane. Use of a carry-on instrument that does not need certification, plus use of the airplane's cabin circulation system to bring in air from outside, avoids these costs.

In accordance with one embodiment, when the sensor 18 detects one of the volcanic gases at a concentration higher than some user-specified threshold, a processor incorporated in that gas sensor issues an activation signal to an alarm device 20 via a data link 22. Preferably the threshold is set at a level below a gas concentration that would be harmful to an airplane passenger or crew member and below a gas concentration that would be found within the volcanic (ash) plume. In other words, its is important that the alarm be activated at a gas concentration that is lower than a level harmful to humans and lower than any level within the boundary space of the volcanic (ash) plume.

In response to reception of the activation signal, the alarm device 20 generates a warning or alarm that is perceptible by the pilot. The alarm device 20 may comprise a display for generating a visual alarm or an annunciator for generating an audible alarm. Optionally, the measured gas concentration may be displayed on a cockpit display using alphanumeric symbols.

In accordance with other embodiments, a respective alarm activation signal may be issued by the processor of each gas sensor that measures a concentration of a respective volcanic gas which is higher than a respective user-specified threshold.

In response to reception of each activation signal, the alarm device 20 generates respective alarms identifying the volcanic gases having concentrations exceeding their thresholds.

Alternatively, a hand-portable unit can be employed comprising one or more gas sensors and an associated alarm device, the unit being configured to be carried on and off an airplane by crew members and stowed in the cockpit at a location exposed to circulating air flow. The use of a hand-portable unit has the advantage that the systems onboard the aircraft need not be configured to issue an alarm in response to an activation signal issued by a gas sensor.

Figure 2:
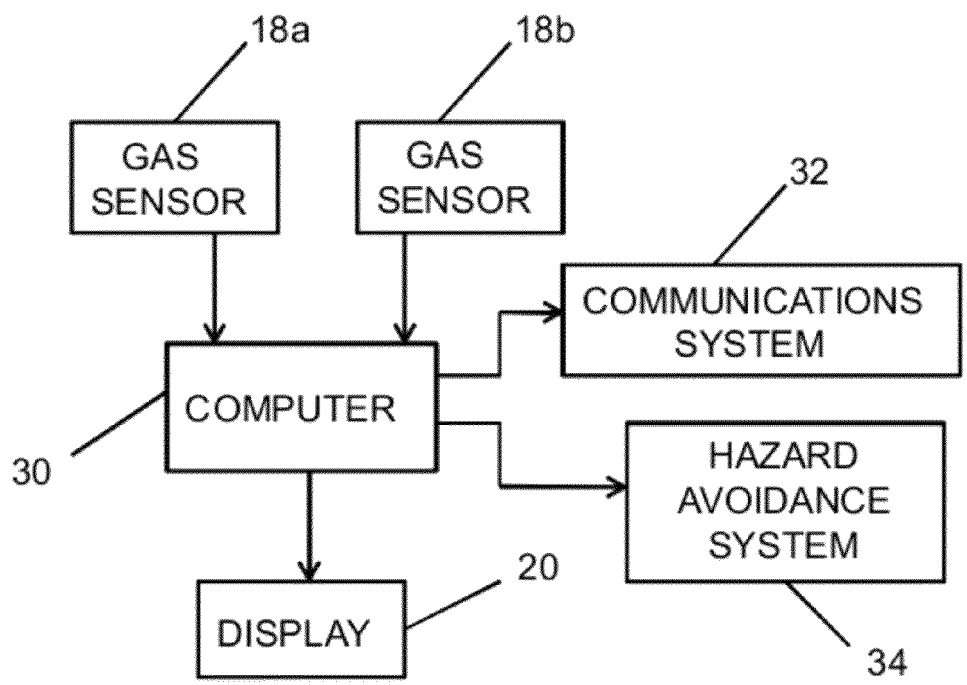
FIG. 2 is a block diagram showing components of a system in accordance with another embodiment of the invention.

In a preferred embodiment depicted in FIG. 2, an ensemble of two or more gas sensors (only two gas sensors 18a and 18b are shown in FIG. 2) is augmented with a computer 30 that monitors the measured gas concentrations over time. The computer 30 executes a pattern recognition algorithm which compares observed gas concentrations as a function of time to expected gas concentrations as a function of time for gases released in a volcanic eruption. (Because an airplane cruises much faster than gases diffuse, time can be used as a proxy for the aircraft position relative to a plume.) When the computer recognizes a pattern with an assurance that exceeds a user-specified confidence level, the computer sends an activation signal to the alarm device 20, which is depicted in FIG. 2 as being a display located, e.g., in the cockpit.

Various further examples will now be disclosed in explanation of how pattern recognition can be used. For the first example, assume that a volcano continuously releases a mixture of gases into the air at a single point. Each volcanic gas diffuses outward from that point at a rate proportional to that gas's diffusion coefficient. In addition, the wind carries the gases downstream. The result is a cone-shaped volcanic (ash) plume and a set of cone-shaped gas plumes concentric therewith, with the narrower central gas plumes consisting of slow-diffusing gases, such as $SO_2$, and the wider outer gas plumes of fast-diffusing gases, such as $H_2$. This is illustrated in FIG. 3, wherein the pair of triangular areas 26 represent a relatively wider cone of diffused hydrogen gas (with the shading in areas 26 indicating decreasing $H_2$ concentration in the wind direction) and the triangular area 28 between areas 26 represents a relatively narrower cone of diffused hydrogen sulfide gas (with the shading in area 28 indicating decreasing $H_2S$ concentration in the wind direction), and wherein the concentric circles show the relative diffusion of hydrogen and hydrogen sulfide gases from particular points in the airstream as those points are carried downwind from the volcano 24.

Figure 3:
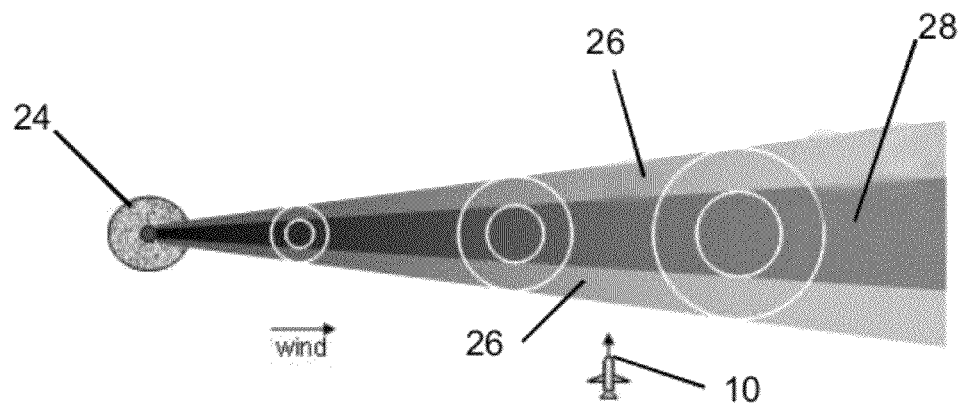
FIG. 3 is a diagram (not to scale) showing the lateral spread of volcanic gases following a volcanic eruption in accordance with a model, wherein highly diffusive gases (e.g., $H_2$) spread faster and form wider downwind plumes than less diffusive gases (e.g., $H_2S$).
Figure 4:
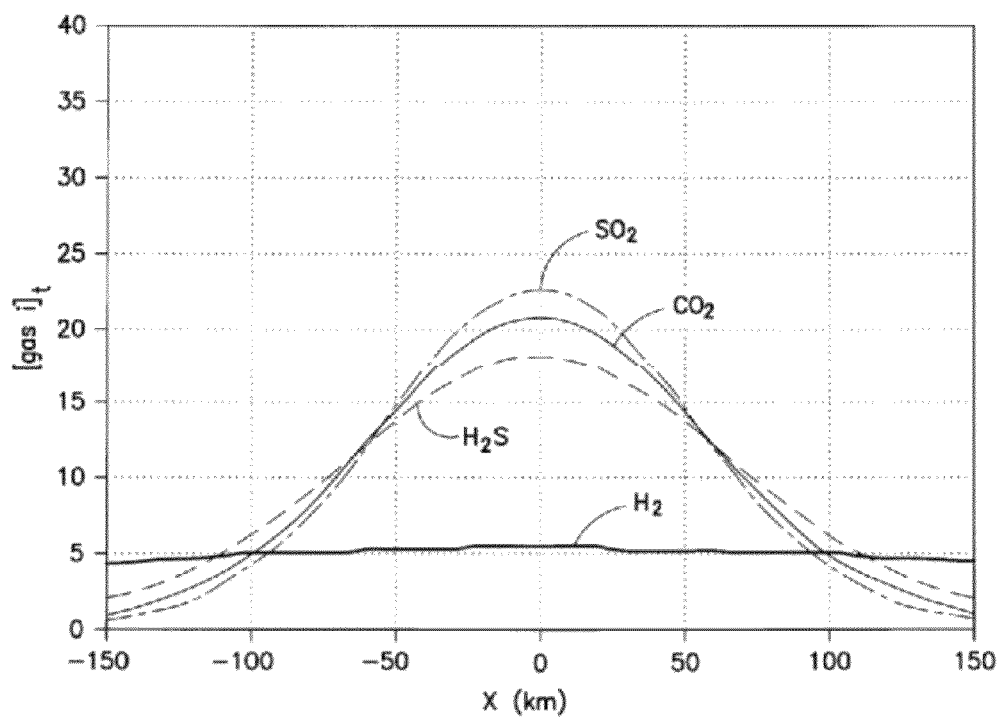
FIG. 4 is a graph showing estimated concentrations of various volcanic gases versus minimum distance x from the axis of a volcanic plume at a distance 300 km downwind from the volcano.

It should be appreciated that the situation depicted in FIG. 3 is idealized: gas plumes do not have smooth boundaries like those shown in FIG. 3. The gas concentrations follow roughly Gaussian distributions, as shown in FIG. 4. In FIG. 4, $[gas\ i]_t$ it is the concentration of gas i at time t. Typically, a set of measurements taken within a few minutes or even a few hours will give relatively smooth curves like the curves seen in FIG. 4, but measurements scattered over longer time periods will not. Measurements widely separated in time cannot be used effectively.

As seen in FIG. 4, hydrogen has a very broad distribution; in the case shown, its mean diffusion distance after time t is comparable to the mean distance it blows downwind in the same time. The heavier gases have narrower distributions. The relative abundance of the gases varies depending on the volcano, but the diffusion coefficient of each gas is constant (aside from predictable factors like air density and temperature) and therefore the shape of each gas's distribution in space and time is constant for a given set of meteorological conditions.

When an aircraft flies through a volcanic plume, it encounters the fast-diffusing gases first, then the slow-diffusing gases, and finally (if it crosses the gas plume) exits the slow-diffusing gas region and returns to a region dominated by fast-diffusing gases. In accordance with one embodiment of the invention, the computer 30 (see FIG. 2) receives measurements from one or more gas sensors (18a, 18b, etc) of the concentrations of respective volcanic gases at multiple points in time. The computer 30 compares these profiles of gas concentration versus time to computer models that predict gas concentrations versus time, given various combinations of factors such as the volcano location, the maximum height of the volcanic (i.e., ash) plume (which varies depending on weather and on the power of the eruption), atmospheric wind profiles, and current aircraft location, speed, heading, and altitude. The computer 30 is programmed with pattern recognition software, as previously described. When the computer 30 determines that the measured gas concentration profile as a function of time matches one of the computer models to a degree that exceeds a user-specified confidence level, the computer issues an activation signal to the alarm device 20 and reports the volcanic (ash) plume parameters from the computer model that was the closest fit to the measured data. The parameters of the best-fit model of the volcanic plume can be displayed on a cockpit display and/or sent to a ground-based central processing site by a communications system 32 (comprising, e.g., a transmitter and transmitting antenna) onboard the aircraft.

It should be apparent that in the situation where the aircraft is flying through a portion of a diffused gas plume and is headed toward but has not yet entered the volcanic (i.e., ash) plume, it would be desirable for the computer 30 to be programmed so that it will recognize an initial increase in the measured concentration of a fast-diffusing volcanic gas above a first threshold followed at a later time by an increase in the measured concentration of a slow-diffusing volcanic gas above a second threshold. Upon recognition of such a pattern, the computer 30 would activate the alarm, hopefully before the aircraft enters the ash plume.

In accordance with a further embodiment, the computer 30 can be connected to a hazard avoidance system 34 (see FIG. 2) that reports which aircraft maneuvers are likely to minimize exposure to ash and toxic gases while remaining within the aircraft's safe acceleration envelope. The basic structure and operation of a suitable hazard avoidance system that could be adapted to avoid a volcanic plume is disclosed in U.S. Pat. No. 7,689,328, the disclosure of which is incorporated by reference herein in its entirety. U.S. Pat. No. 7,689,328 discloses a system which uses information about the aircraft, weather, and physical obstacles to automatically generate a series of maneuvers to safely reach an emergency landing site when an aircraft loses power. A route analysis and planning tool utilizes a routing algorithm to process information from a combination of geographic data, global positioning system (GPS) data, aircraft-instrumentation data, and performance parameters. The route analysis and planning tool may also display route data to the pilot.

In accordance with the foregoing volcanic plume avoidance embodiment, the computer 30 can be provided with software for generating a hazard model which, e.g., would fit gas concentration measurements to a conical plume model and use the cone parameters to estimate the surface or boundary beyond which ash or gas would be dangerous. This hazard model would then be input into the system disclosed in U.S. Pat. No. 7,689,328 as a physical obstacle, and the latter system would automatically generate a series of safe maneuvers to avoid the physical obstacle posed by the modeled volcanic (ash) or toxic gas plume.

Figure 5:
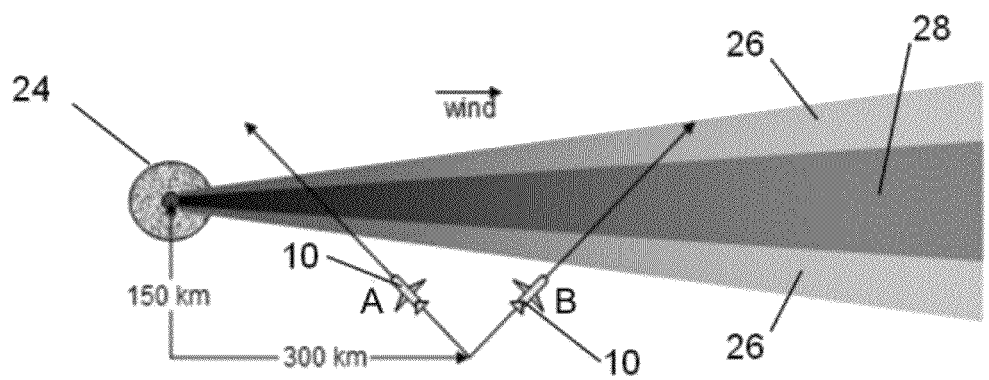
FIG. 5 is a diagram (not to scale) showing an aircraft approaching a volcanic plume on two different headings (indicated by arrows respectively designated A and B) from a position 300 km downwind of the volcano and 150 km from the plume axis.

FIG. 5 shows other exemplary aircraft encounters with concentric plumes of volcanic gases. In both cases, the aircraft 10 approaches the plume from an initial position 300 km downwind of the volcano 24 and 150 km from the volcanic plume's axis. The aircraft on path A flies a heading 135° from the plume's axis. The aircraft on path B flies a heading 45° from the plume's axis.

Figure 6:
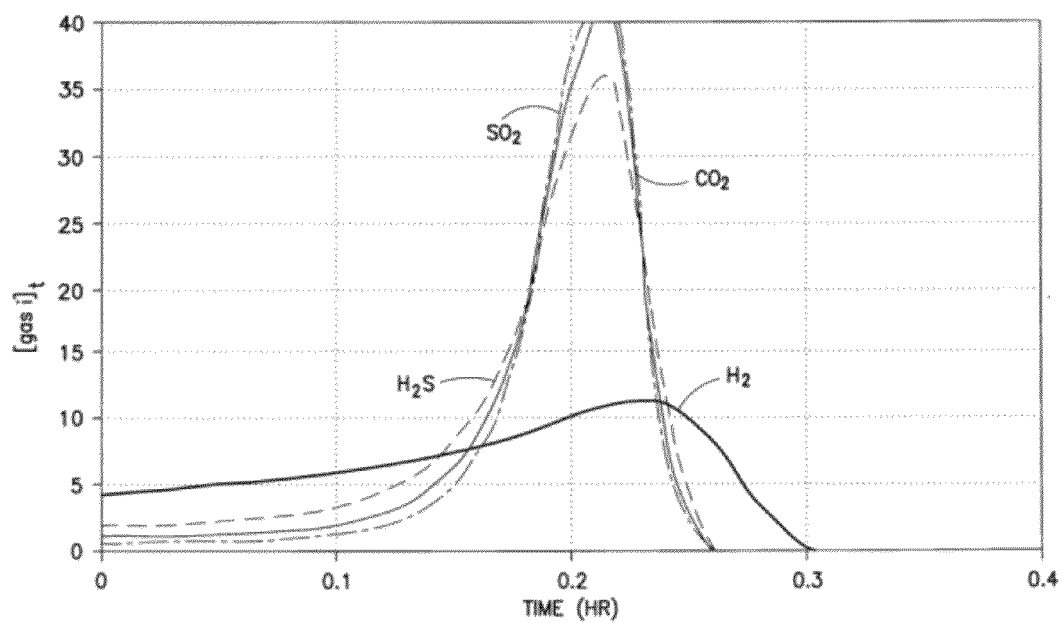
FIGS. 6 and 7 are graphs showing estimated concentrations of various volcanic gases versus time as an aircraft flies through the volcanic gas plumes. The graph in FIG. 6 is for an aircraft heading 135 degrees from the plume axis (indicated by arrow A in FIG. 5), whereas the graph in FIG. 7 is for an aircraft heading 45 degrees from the plume axis (indicated by arrow B in FIG. 5)
Figure 7:
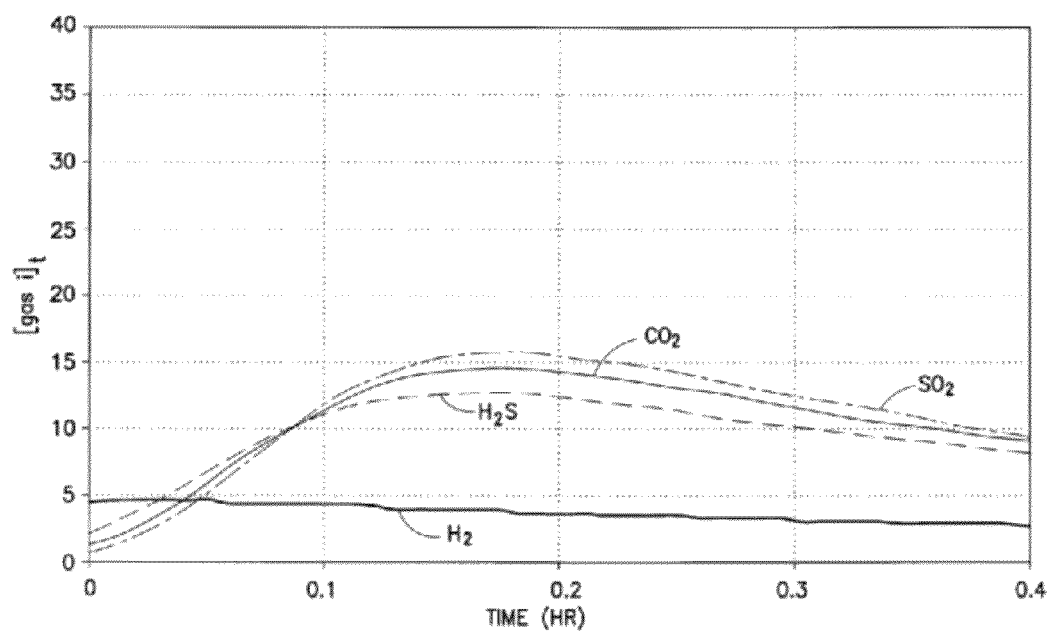

The corresponding profiles of gas concentrations versus time for flight paths A and B (see FIG. 5) are shown in FIGS. 6 and 7. The plot in FIG. 6 (for a flight path at an angle of 135° relative to the plume axis) shows a rapid percentage rise in each of the slow-diffusing gases, indicating that the aircraft is approaching a region where the gases are concentrated in a relatively small volume. This is what would be expected given that path A is headed generally upwind, where the volcanic plume is relatively narrow and gas concentrations are high—path A crosses the common axis of the gas plumes 26 and 28 only 150 km downwind of the volcano 24. Concentration of the heaviest gas, sulfur dioxide, peaks slightly before the concentration of carbon dioxide and hydrogen sulfide, all of which reach peak concentrations much earlier than hydrogen. This is because the heavier gases remain concentrated near the plume axis, while (in the case modeled here) hydrogen diffuses so rapidly that its concentration is affected more by distance from the volcano itself than by distance from the plume axis.

The plot in FIG. 7 (for a flight path at an angle of 45° relative to the plume axis) shows a much slower percentage rise in the slow-diffusing gases and reaches much lower peak concentrations. This is consistent with crossing the plume axis 450 km downwind of the volcano where the volcanic plume is wide and gas concentrations are low. Hydrogen concentration peaks earlier than the heavier gas concentrations.

These example profiles are for two specific paths approaching a specific, simple volcanic plume. Those skilled in the art will appreciate that real plumes of volcanic gas may have more complex concentration profiles due to a variety of meteorological and orographic details, but that these details can be modeled sufficiently well to give good predictions of gas concentration profiles at cruise altitudes within a few hours of a volcanic eruption, and that modern pattern-recognition algorithms can discriminate between measured concentration profiles corresponding to substantially different real plumes of volcanic gas.

More sophisticated embodiments of the present invention may include the following elements:

a computer further programmed to use (a) current aircraft location, speed, heading, and/or altitude, (b) estimated winds aloft, and (c) the best match between measured gas concentration patterns and computer-modeled gas concentration patterns to estimate at least one of the following parameters: volcano location, maximum height of the ash plume or a toxic gas plume, and rate of gas release for any of the four gases identified above; and to estimate the location, orientation, and width of the ash plume or toxic gas plume corresponding to those parameters;

means to display (e.g., a cockpit display) at least one of the volcano location, maximum height of the ash plume or a toxic gas plume, and rate of gas release for any of the four gases identified above; or a plume location, orientation, and width corresponding to those parameters; and a communications system by which information about the absence or presence of a plume, and potentially its characteristics, can be transmitted to other aircraft, air traffic controllers, or meteorologists.

In a case where an aircraft is approaching a volcanic plume that could have arisen from at least two mutually exclusive situations, the systems and methods disclosed herein must determine which situation is occurring before it can estimate the characteristics of a plume. For example, assume that an airplane is cruising over a region such as Indonesia or Alaska that contains many potentially active volcanoes, and that the airplane encounters rising concentrations of volcanic gases. Before the system can estimate the range to a point of interest along a volcanic plume's axis or on the outer surface or boundary of a volcanic plume (e.g., the point where the aircraft will intersect the boundary of the volcanic plume if the aircraft were to continue on its present course), it may be helpful to classify the event, i.e., identify which volcano is the likely source of the eruption. Pattern recognition is useful for classifying a set of observations as belonging to one of a set of mutually exclusive classes.

One method for using pattern recognition comprises the following steps: (1) given recent weather data and the locations of known volcanoes, run a plume propagation model for each of the known volcanoes (or a Monte Carlo set of propagation models, if the recent weather is not well known); (2) use the outputs of the model to calculate gas concentrations at points along the aircraft's path; (3) train an artificial neural network to recognize which volcano produced a given gas plume; (4) use the artificial neural network to classify the actual measurements as belonging to one particular volcano; and finally (5) given a particular volcano as the gas plume source, apply other methodologies to estimate the characteristics of the ash and/or gas plumes. This approach uses a model-trained artificial neural network for pattern recognition. However, many other well-known pattern recognition algorithms can be used, such as naive Bayes classifiers and k-nearest neighbor algorithm decision rules.

Although the embodiments disclosed so far involve measurements made on a single airplane, some embodiments of the invention use measurements made aboard multiple aircraft, the measurement data being relayed to a ground-based central processing site. The central processing site comprises a computer that combines the measurements from all aircraft, together with locations and times at which the measurements were made, meteorological data, and information about plausible volcanic sites, to better estimate the location and other characteristics of the ash and/or gas plumes.

In particular, the central processing site may comprise a data fusion system that receives gas concentration measurements from multiple aircraft and combines them to form an improved estimate of a plume's characteristics and, optionally, construct a three-dimensional model of the plume. In this case, each of a plurality aircraft transmits a respective set of gas concentration measurements (and associated metadata, such as time and location of the aircraft) to a data fusion center via a network. More specifically, each aircraft comprises a transmitter and an antenna for wireless communication with the network. All measurements are incorporated into the data fusion system and are used to detect the presence of a volcanic plume and estimate the plume's characteristics. Optionally, the data fusion system also constructs a three-dimensional model of the plume. When the measured gas concentrations from multiple aircraft indicate the presence of a volcanic plume, the data fusion system generates a warning to a human controller, e.g., a visual warning which is displayed by a controller warning display. The particular fusion algorithm or approach may vary.

There are several known hardware/software systems that combine observations of phenomena from multiple mobile sensors to create a better estimate than any single sensor could make on its own. Two examples are the following:

Meteorological measurements from diverse balloons and aircraft are transmitted via radio links and ground networks to a workstation. The workstation runs a software program called 4DVAR, which uses a variational cost-minimization approach to fuse data from multiple sensors at various times and places. (A technical summary of the 4DVAR method can be found at http://www.ecmwf.int/newsevents/training/rcourse_notes/DATA_ASSIMILATION/ASSIM_CON-CEPTS/Assim_concepts11.html, the contents of which are incorporated by reference herein in its entirety.) Its output is an atmosphere model that is more accurate than an analysis could produce from a lone sensor.

Military radar observations from multiple ground and airborne radars are transmitted via various networks to a workstation. The workstation runs a Bayesian software model that combines evidence from various radar measurements to accurately track a hostile aircraft.

These methods are well known to persons skilled in the art of data fusion. Compared to the general meteorology case, in which many different kinds of data are combined, the problem of transmitting and combining gas concentration measurements (a single kind of data) from different aircraft should not require undue experimentation by persons skilled in the art.

Installing the invention on multiple aircraft that communicate with a network improves the chance to detect and characterize a volcanic plume before it damages any aircraft. A warning signal from the first aircraft to detect the plume can be relayed to all aircraft in the area, even those without the invention.

Because various embodiments of a detection system can measure the concentrations of two or more volcanic gases, the system enables robust detection of the proximity of an ash plume from any volcano. Carbon dioxide is present at a background level of about 390 parts per million by volume in non-volcanic air. The background level of hydrogen is about 0.55 ppm. Hydrogen sulfide and sulfur dioxide normally occur at less than 0.1 ppm. It is hard to imagine any event that would introduce a significant amount of the last three of these gases into the air at cruise altitude. Therefore, detecting even a tiny amount of any of the last three gases at cruise altitude is a reliable indicator of a volcanic plume.

Analysis of the diffusion patterns of the four volcanic gases reveals that those diffusion patterns lead to quite distinct profiles of gas concentration versus time, depending on how an aircraft approaches a volcanic plume. Distinguishing between these profiles is well within the capability of modern pattern-matching algorithms.

As previously disclosed, in accordance with some embodiments, the detection system invention can be quickly and cheaply added to existing aircraft by simply carrying it onboard. This offers a faster, cheaper response to fears of volcanic plumes than any device that must be affixed to the outside of an airplane. Attachments on the outside require FAA certification to show that (a) any changes to the airflow are safe and (b) the device will not break loose and damage an engine or endanger people on the ground. Further certification costs arise if an externally-mounted device requires a hull penetration, e.g. for a power cable.

In summary, the embodiments disclosed herein provide distinct advantages as compared to prior solutions for detecting the presence of a volcanic plume.

First, seeing and avoiding the plume does not work when volcanic ash plumes cannot be seen, e.g., at night or when the plume is embedded in other clouds. The disclosed embodiments do not rely on visual contrast. Instead, it directly measures gas concentrations associated with volcanic plumes. Therefore, it detects plumes embedded in other clouds and detects plumes at night when sunlight or moonlight may be insufficient.

Second, the disclosed embodiments do not rely on geological sensors or human observation of volcanoes, so it can detect plumes from remote, un-instrumented volcanoes.

Third, the disclosed embodiments continuously measure gas concentrations around the aircraft. A modern infrared spectrometer can make a measurement every ten seconds, with worst-case total delay less than 20 seconds from air intake to reported analysis. This shortens the average warning time by a factor of about 10,000 compared to reliance on overhead passes by specially equipped sensing satellites.

Furthermore, the embodiments disclosed herein provide direct warning to an airplane's pilot rather than relying on the process to issue a notice to airmen.

While the invention has been described with reference to various embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention.

As used in the claims, the term "volcanic plume" means a plume of volcanic ash.

The invention claimed is:

1. A method for detecting volcanic gases, comprising the following steps:
    (a) measuring the concentration of one or more volcanic gases in air circulating in a space inside the aircraft; and
    (b) generating a perceptible alarm when one or more measured volcanic gas concentrations exceed a respective user-specified threshold or when a pattern of volcanic gas concentration is recognized with a user-specified confidence level.

2. The method as recited in claim 1, wherein said threshold or confidence level is set such that said alarm indicates the proximity of a dangerous level of either volcanic gas or volcanic ash.

3. The method as recited in claim 1, further comprising the following steps:
    outputting electronic data representing the measured concentration of said volcanic gas;
    processing said electronic data representing the measured concentration of said volcanic gas; and
    issuing an activation signal when the measured concentration of said volcanic gas exceeds a specified threshold,
    wherein said generating step comprises generating a perceptible alarm in response to issuance of said activation signal.

4. The method as recited in claim 1, wherein said space inside said aircraft is a cabin.

5. The method as recited in claim 1, wherein said space inside said aircraft is a cockpit.

6. The method as recited in claim 1, further comprising the steps of carrying a hand-portable unit onboard the aircraft and placing the hand-portable unit in a location where it is exposed to incoming cockpit air or cabin air, wherein said hand-portable unit performs steps (a) and (b).

7. The method as recited in claim 1, wherein the volcanic gases whose concentrations are measured comprise one or more gases selected from the following group: hydrogen, hydrogen sulfide, carbon dioxide, and sulfur dioxide.

8. The method as recited in claim 1, wherein said alarm is audible or visible to a pilot in a cockpit of the aircraft.

9. The method as recited in claim 1, further comprising the step of estimating a parameter of a plume based on the results of step (a).

10. A method for detecting aircraft approach to a volcanic plume, comprising the following steps:
(a) measuring the concentration of one or more volcanic gases in air circulating in a space onboard an aircraft during flight;
(b) storing the measured concentrations in memory as a function of time;
(c) storing expected concentrations of said one or more of said volcanic gases in memory as a function of time;
(d) for each volcanic gas for which the concentration has been measured, comparing a respective measured concentration as a function of time with a respective expected concentration as a function of time; and
(e) activating an audible or visible alarm in response to the measured concentration as a function of time of one of said volcanic gases matching to a sufficient degree the corresponding expected concentration as a function of time of said one of said volcanic gases or in response to the measured concentrations as a function of time of more than one of said volcanic gases being similar to at least a specified degree to the corresponding expected concentrations as a function of time of said more than one of said volcanic gases.

11. The method as recited in claim 10, wherein the volcanic gases whose concentrations are measured comprise one or more gases selected from the following group: hydrogen, hydrogen sulfide, carbon dioxide, and sulfur dioxide.

12. The method as recited in claim 10, further comprising the step of placing a respective hand-portable gas sensor in said space for each volcanic gas whose concentration is to be measured.

13. The method as recited in claim 12, wherein the hand-portable gas sensors are placed near an air inlet by which gas in the atmosphere external to the aircraft enters said space onboard the aircraft.

14. The method as recited in claim 12, wherein said alarm is audible or visible to a pilot in a cockpit of the aircraft.

15. The method as recited in claim 10, further comprising the step of estimating a parameter of a plume based on the results of step (a).

16. An aircraft comprising:
one or more sensors for respectively measuring the concentration of one or more volcanic gases in air circulating inside the aircraft during flight, said one or more volcanic gases being selected from the following group: hydrogen, hydrogen sulfide, carbon dioxide, and sulfur dioxide; and
a device for providing a pilot-perceptible alarm in response to the measured concentration of one of said volcanic gases being above its threshold or in response to the measured concentrations of more than one of said volcanic gases being above their respective thresholds.

17. The aircraft as recited in claim 16, wherein said one sensor comprises a gas chromatograph.

18. The aircraft as recited in claim 16, wherein said one sensor comprises an infrared spectrometer.

19. An aircraft comprising:
one or more sensors for respectively measuring the concentration of one or more volcanic gases in air circulating inside the aircraft during flight, said one or more volcanic gases being selected from the following group: hydrogen, hydrogen sulfide, carbon dioxide, and sulfur dioxide;
a processor programmed to compare a respective measured concentration as a function of time with a respective expected concentration as a function of time for each volcanic gas for which the concentration has been measured and then issuing an activation signal in response to the measured concentration as a function of time of one of said volcanic gases being similar to at least a specified degree to the corresponding expected concentration as a function of time of said one of said volcanic gases or in response to the measured concentrations as a function of time of more than one of said volcanic gases matching to a sufficient degree the corresponding expected concentrations as a function of time of said more than one of said volcanic gases; and
a device for providing a pilot-perceptible alarm in response to issuance of said activation signal.

20. The aircraft as recited in claim 19, wherein said one sensor comprises a gas chromatograph or an infrared spectrometer.

* * * * *